US011813345B2

(12) United States Patent
Wang et al.

(10) Patent No.: US 11,813,345 B2
(45) Date of Patent: Nov. 14, 2023

(54) PERSONAL CARE CLEANING COMPOSITIONS

(71) Applicant: The Procter & Gamble Company, Cincinnati, OH (US)

(72) Inventors: Huan Wang, Singapore (SG); Nadine Susanne Gallitschke-Irvine, Singapore (SG); Gabriel Wei Sheng Liew, Singapore (SG); Jiquan Liu, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 612 days.

(21) Appl. No.: 16/919,415

(22) Filed: Jul. 2, 2020

(65) Prior Publication Data

US 2021/0000724 A1 Jan. 7, 2021

Related U.S. Application Data

(60) Provisional application No. 62/870,815, filed on Jul. 5, 2019.

(51) Int. Cl.
*A61K 8/34* (2006.01)
*A61Q 5/02* (2006.01)
*A61Q 19/10* (2006.01)
*A61K 8/46* (2006.01)
*A61K 8/9761* (2017.01)
*A61K 8/44* (2006.01)

(52) U.S. Cl.
CPC .............. *A61K 8/463* (2013.01); *A61K 8/342* (2013.01); *A61K 8/44* (2013.01); *A61K 8/9761* (2017.08); *A61Q 5/02* (2013.01); *A61Q 19/10* (2013.01); *A61K 2800/59* (2013.01)

(58) Field of Classification Search
None
See application file for complete search history.

(56) References Cited

U.S. PATENT DOCUMENTS

| | | | |
|---|---|---|---|
| 6,194,364 B1 * | 2/2001 | Glenn, Jr. ............. | A61Q 19/10 510/159 |
| 6,323,166 B1 * | 11/2001 | Kamiya ................. | C11D 3/18 510/130 |
| 6,451,333 B1 | 9/2002 | Beerse | |
| 6,566,313 B1 * | 5/2003 | Hohenstein ............. | A61Q 5/12 510/501 |
| 8,840,911 B2 | 9/2014 | Flugge-berendes | |
| 9,050,288 B2 | 6/2015 | Gilbard et al. | |
| 9,247,737 B2 | 2/2016 | Cornmell | |
| 10,624,828 B2 | 4/2020 | Kelly et al. | |
| 2004/0247551 A1 | 12/2004 | Yokomaku | |
| 2005/0053572 A1 | 3/2005 | Hwang | |
| 2014/0274852 A1 | 9/2014 | Jiang et al. | |
| 2015/0173355 A1 | 6/2015 | Konate | |
| 2017/0354177 A1 | 12/2017 | Iohara | |
| 2018/0333339 A1 | 11/2018 | Hamersky | |
| 2019/0000737 A1 | 1/2019 | Kelly et al. | |
| 2020/0078281 A1 | 3/2020 | Wang | |

FOREIGN PATENT DOCUMENTS

| | | |
|---|---|---|
| CN | 1356890 A | 7/2002 |
| CN | 101203272 A | 6/2008 |
| CN | 102088950 A | 6/2011 |
| EP | 1435899 B1 | 3/2009 |
| FR | 2855564 B1 | 4/2007 |
| JP | H11269042 A | 10/1999 |
| JP | H11269043 A | 10/1999 |
| JP | 2003026546 A | 1/2003 |
| JP | 2004091333 A | 3/2004 |
| JP | 2006045126 A | 2/2006 |
| JP | 2007169233 A | 7/2007 |
| JP | 2011261923 A | 12/2011 |
| KR | 20000038214 A | 7/2000 |
| KR | 20070056207 A | 6/2007 |
| KR | 20070074690 A | 7/2007 |
| KR | 100782273 B1 | 12/2007 |
| KR | 101066797 B1 | 9/2011 |
| KR | 101114307 B1 | 2/2012 |
| WO | 2006134160 A2 | 12/2006 |
| WO | WO-2007017760 A2 * | 2/2007 ............. A01N 31/02 |

OTHER PUBLICATIONS

AA1359 PCT Search Report and Written Opinion for PCT/US2020/070231 dated Oct. 23, 2020, 17 pages.
All Office Actions; U.S. Appl. 16/125,940, filed Sep. 10, 2018.

* cited by examiner

*Primary Examiner* — Robert T. Crow
*Assistant Examiner* — John P Nguyen
(74) *Attorney, Agent, or Firm* — Alexandra S. Anoff

(57) ABSTRACT

Certain liquid personal care cleaning compositions containing: linalool, a linalool isomer, or combinations thereof; and hinokitiol exhibit effective antibacterial properties.

20 Claims, No Drawings

PERSONAL CARE CLEANING COMPOSITIONS

FIELD OF THE INVENTION

The present invention relates to liquid personal care cleaning compositions with anti-bacterial properties.

BACKGROUND OF THE INVENTION

Liquid personal care cleaning compositions are well known. Users have come to expect lots of foam to signal good cleaning. These compositions generally contain a relatively high level of surfactant, e.g., greater than 4 wt % for cleaning and sudsing benefits. One popular class of surfactants for such compositions include alkyl sulfates. These compositions typically have a slightly acid to acidic pH because human skin is generally regarded as having a pH between 5-6.

Anti-bacterial benefits are an important benefit for many users, especially for hand cleaning composition. Many geographic markets have requirements to support fast acting germ/antimicrobial efficacy benefits. For example, the P.R. China's GB15979 method is a national standard to support advertising claims directed to disinfection or sanitary products for fast germ inhibition (GB15979-C4) or fast germ kill (GB15979-C3). In parallel, the Ministry of Health of P.R. China also published a "Technical Standard For disinfection" regulation in 2002 to guide and define the test standards to assess fast antimicrobial efficacy. Classic preservatives, such as benzyl alcohol, do not materially contribute to such fast reacting efficacy benefits.

There is a continuing need to find safe and effective ingredients for use in personal care cleaning compositions that contribute to fast acting antimicrobial efficacy benefits but minimize negatives effects. Hinokitiol is an efficacious molecule. However, it is generally expensive and if used alone simply does not have enough of fast acting antimicrobial impact. Linalool (and some of its isomers) are well known perfume raw materials that have been reported to generally have weak antimicrobial activity. However, used alone, linalool will not have enough fast-acting antimicrobial effect. The dosage of linalool needs to be relatively high to deliver reasonable efficacy, but this poses the additional challenge of solubility in liquid aqueous formulation chassis. And if used at high levels, linalool may also provide scent profiles that are too strong or undesirable for some consumer segments. The use of diol alcohols (greater than about 1%) has been reported to facilitate the solubilization of linalool in some water containing formulations. However, such diol alcohols may negatively impact on rheology, foaming properties, and/or chassis stability.

There is a need for a liquid aqueous personal care compositions that provide user desired foaming, are effective at cleaning skin and hair and the like, have a slightly acidic to acidic pH, and provide fast acting antimicrobial efficacy benefits (e.g., meeting regulatory requirements of China).

SUMMARY OF THE INVENTION

A synergistic combination of linalool or linalool isomers in combination with hinokitiol in liquid personal care cleaning compositions exhibiting fast acting anti-microbial effects is surprisingly found. Accordingly, one aspect of the present invention provides for the liquid personal care cleaning composition comprising: greater than 4 wt % of at least one surfactant; greater than 0.8 wt % to 2.0 wt % of the combination of: (i) linalool, a linalool isomer, or combinations thereof; and (ii) hinokitiol; and wherein the weight:weight ratio of said linalool, linalool isomer(s), or combinations thereof to said hinokitiol is less than 18:1, respectively. Preferably the composition has a pH less than 7. Another aspect of the invention provides for a method of reducing bacteria on a surface comprising the step of contacting the surface with the aforementioned composition.

The compositions described herein may have one or more advantages. One advantage is minimizing the use of diol alcohols (such as propylene glycol, ethylene glycol, and isopropylene glycol) to help avoid formulation complexity (e.g., perhaps a negative impact on rheology). Another advantage is the use of alkyl sulfate surfactants to help with foaming. Another advantage is a preferred slightly acidic to acidic pH range to help to reflect the pH of the target surface to be cleaned (e.g., skin). Another advantage of the compositions described is passing standards methods, especially in China, to demonstrate fast acting antimicrobial efficacy benefits. Another advantage of the compositions described is minimizing negatives and/or formulation complexity.

These and other features of the present invention will become apparent to one skilled in the art upon review of the following detailed description when taken in conjunction with the appended claims.

DETAILED DESCRIPTION OF THE INVENTION

Definitions

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt %" herein. All molecular weights as used herein are weight average molecular weights expressed as grams/mole, unless otherwise specified.

As used herein, the articles including "a" and "an" when used in a claim, are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

Fast Acting Anti-Microbial Effects Synergy in providing fast acting anti-microbial benefits to liquid personal care cleaning composition is observed. These compositions contain greater than 0.8 wt % to 2.0 wt % of the combination of: (i) linalool, a linalool isomer, or combinations thereof; and (ii) hinokitiol. Linalool is identifiable by its IUPAC name 3,7-Dimethyl-1,6-octadien-3-ol (CAS Nos. 78-70-6; 126-91-0; 126-90-9). Isomers of linalool include nerol and geraniol. In one example, the composition comprises said geraniol, nerol, and combinations thereof. Nerol is identifiable by its IUPAC name (Z)-3,7-dimethyl-2,6-octadien-1-ol (CAS No. 106-25-2). Geraniol is identifiable by its IUPAC name (2E)-3,7-Dimethyl-2,6-octadien-1-ol (CAS No. 106-24-1). Hinokitiol is identifiable by its IUPAC name 2-Hydroxy-6-propan-2-ylcyclohepta-2,4,6-trien-1-one (CAS No. 499-44-5).

An additional aspect of the composition includes a weight:weight (wt:wt) ratio of the linalool, linalool isomer(s), or combinations thereof to the hinokitiol that is less than 18:1, respectively. Preferably this wt:wt ratio is from less than 15:1, more preferably 13:1 to 1:1, yet more preferably from 12:1 to 5:1, yet still more preferably from 11:1 to 7:1, alternatively from 10:1 to 8:1.

One way of assessing fast acting anti-microbial effects is by reducing $E.\ coli$ ATCC25922 bacteria within 2 min per P.R. China's Technical Disinfection Test method (published in 2002), preferably by more than 1 log reduction of said bacteria, yet more preferably 2 log reduction of said bacteria. Bacteria can be reduced by contacting a surface with a composition described herein. The subject surface may include skin, hair, or a combination of skin and hair.

Preferably the compositions herein comprise greater than 0.05 wt % of hinokitiol, preferably greater than 0.09 wt %, more preferably at least 0.1 wt %, yet more preferably from at least 0.1 wt % to 0.5 wt % of hinokitiol. Preferably compositions herein comprise at least 0.05 wt % but less than 1 wt % hinokitiol, preferably less than 0.5 wt %, more preferably less than 0.3 wt %. The composition comprises at least 0.1 wt % of linalool, a linalool isomer, combinations thereof, preferably from at least 0.5 wt %, more preferably from at least 0.75 wt %, even more preferably at least 0.8 wt % to less than 1.2 wt % of said linalool, a linalool isomer, or combinations thereof.

pH

The compositions have a pH less than 7. Preferably the pH is less than 6, preferably the pH from 4 to 5.2, more preferably from pH 4 to 5, yet more preferably from pH 4.2 to 4.5. In one example, the pH is from 4.1 to 4.7. The addition of citric acid to the composition is one example of how the pH of the composition can be modified.

Surfactant

The compositions of the present invention comprise greater than 4 wt % of at least one surfactant. Surfactant(s) can generally present in an amount of 5 wt % to 50 wt %. The surfactants can be, for example, linear, sulfate surfactants. Examples of such surfactants include sodium lauryl sulfate or ammonium lauryl sulfate in which these materials do not contain any ethoxylation or propoxylation. Additional surfactants include sodium laureth sulfate or ammonium laureth sulfate in which the materials contain a level of ethoxylation and/or propoxylation. Examples of such surfactants include sodium laureth-1 sulfate, sodium laureth-2 sulfate, sodium laureth-3 sulfate, ammonium laureth-1 sulfate, ammonium laureth-2 sulfate, or ammonium laureth-3 sulfate. Such materials can be described as SLEnS or ALEnS in which n is the average number of moles of ethoxylation and/or propoxylation. The surfactant may also be a branched anionic surfactant. Examples of some suitable branched anionic surfactants include: sodium trideceth sulfate, sodium tridecyl sulfate, sodium C12-13 alkyl sulfate, sodium C12-15 alkyl sulfate, sodium C11-15 alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, sodium $C_{12-14}$ pareth-n sulfate, and combinations thereof. Other salts of all the aforementioned surfactants are useful, such as TEA, DEA, ammonia, potassium, and sodium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, TX; from synthetic alcohols such as Neodol™ 23 Alcohol available from Shell Chemicals, USA; from synthetically made alcohols such as Safol™ 23 and Neodol™ 23. Suitable examples of alkoxylated alcohols are Safol™ 23-3 and Neodol™ 23-3. Another example of an anionic surfactant is $C_{10}$-$C_{24}$ acyl glycinate salt (preferrably sodium cocoyl glycinate (obtained from glycine and coconut fatty acids)).

The surfactant may also be STnS, wherein n can define average moles of ethoxylation. A structured cleaning phase can include from 5% to 20%, from 7% to 18%, from 5% to 10%, from 9% to about 16%, from 11% to 14%, by weight of the composition, of STnS, wherein n can range from 0 to 3, from 0.5 to 3, from 1.1 to 3.

Another anionic surfactant which can be used herein can is acyl glutamate. In one example, the acyl glutamate comprises a $C_{10}$-C14 acyl glutamate. The acyl glutamate can have one or more cations selected from the group consisting of sodium, potassium, ammonium, substituted ammonium, and any combinations thereof. For example, the compositions may comprise less than 5% sodium lauryl sulfate (SLS), less than 4% SLS, less than 3% SLS, less than 2% SLS, less than 1% SLS, between 0.1% SLS and 2% SLS, or 0% SLS, by weight of the composition.

The surfactant may also comprise cationic surfactants, nonionic surfactants, amphoteric surfactants, zwitterionic surfactants, and mixtures thereof. For example, the composition comprises at least one amphoteric surfactant and/or at least one zwitterionic surfactant. Amphoteric surfactants suitable for use herein can include those that are broadly described as derivatives of aliphatic secondary and tertiary amines in which the aliphatic radical can be straight or branched chain and wherein one of the aliphatic substituents contains from 8 to 18 carbon atoms and one contains an anionic water solubilizing group, e.g., carboxy, sulfonate, sulfate, phosphate, or phosphonate. Examples of compounds falling within this definition include sodium 3-dodecyl-aminopropionate, sodium 3-dodecylaminopropane sulfonate, sodium lauryl sarcosinate, N-alkyltaurines such as the one prepared by reacting dodecylamine with sodium isethionate, and N-higher alkyl aspartic acids. For example, the composition can comprise an amphoteric surfactant that is selected from the group consisting of sodium lauroamphoacetate, sodium cocoamphoacetate, disodium lauroamphoacetate, disodium cocodiamphoacetate, and mixtures thereof. Moreover, amphoacetates and diamphoacetates can also be used. Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from 8 to 18 carbon atoms and one contains an anionic group, e.g., carboxy, sulfonate, sulfate, phosphate, or phosphonate. Zwitterionic surfactants 5 suitable for use in the composition include betaines, including, for example, cocoamidopropyl betaine and laurylamidopropyl betaine. Cationic surfactants can include those broadly described as surfactant with the surface active portion bears a positive charge. The major classes of the cationics are a salt of long-chain amine or quaternary ammonium chloride or bromide. Examples of this class include behentrimonium chloride, benzalkonium chloride, benzethonium chloride, benzododecinium bromide, carbethopendecinium bromide, cetalkonium chloride, cetrimonium bromide, cetrimonium chloride, cetylpyridinium chloride, didecyldimethylammonium chloride, dimethyldioctadecylammonium bromide, dimethyldioctadecylammonium chloride, tetramethylammonium hydroxide, and mixtures thereof. The nonionic surfactant may be, for example, an alkyl polyglycoside. The composition may also comprise a combination of alkyl polyglycoside and acyl glutamate.

Preferably the liquid personal care cleaning compositions herein comprise greater than 4 wt % of at least one surfactant, preferably from 5 wt % to 25 wt %, more preferably greater than 7 wt %, yet more preferably from 8 wt % to 12 wt % of the at least one surfactant.

In one example, the at least one surfactant comprises at least a first alkyl sulfate surfactant and a second alkyl sulfate surfactant. Preferably the first alkyl sulfate surfactant is sodium lauryl sulfate ("SLS"). Preferably second alkyl sulfate surfactant is alkyl ether sulfate, preferably the alkyl ether sulfate is sodium laureth 3 sulfate ("SLES"). Preferably the composition comprises from 0.01-10 wt %, preferably 1-3 wt %, of the first alkyl sulfate surfactant. Preferably the composition comprises from 0.01-20 wt %, preferably 4-10 wt %, of the second alkyl sulfate surfactant.

In one example, the at least one surfactant comprises at least an alkyl sulfate surfactant. Preferably wherein the alkyl sulfate surfactant is alkyl ether sulfate, preferably wherein the alkyl ether sulfate is sodium laureth 3 sulfate ("SLES"). Preferably the composition comprises from 0.01-20 wt %, preferably 4-10 wt %, of the alkyl sulfate surfactant.

In one example, the at least one surfactant further comprises a betaine, preferably a cocamidopropyl betaine. Preferably the composition comprises 0.01-10 wt %, preferably 0.1 to 4 wt %, of said betaine, preferably the said betaine is cocamidopropyl betaine.

Structuring System

The compositions herein may also comprise a structuring system wherein the structuring system can comprise an associative polymer, a non-associative polymer, an electrolyte, trihydroxystearin, and combinations thereof. The structuring system can comprise from 0.05% to 5%, from 0.05% to 1%, from 0.07% to 0.5%, or from 0.1% to 0.3%, by weight of the composition, of a structuring material such as a nonassociative polymer. The structuring system can comprise from 0.001% to 5%, from 0.005% to 0.5%, from 0.007% to 0.05%, from 0.008% to 0.04%, or from 0.01% to 0.03%, by weight of composition, of an associative polymer.

As noted herein, stability of a composition can be maintained or enhanced even with the reduction of associative polymer with the addition of a non-associative polymer. The composition may comprise from 0.05% to 5%, from 0.05% to 1% by weight of the composition, of a structuring material selected from the group consisting of an associative polymer, Trihydroxystearin, or combinations thereof.

An exemplary associative polymer can include AQUPEC® SER-300 made by Sumitomo Seika of Japan, which is an acrylate/$C_{10}$-$C_{30}$ alkyl acrylate cross-polymer and comprises stearyl side chains with less than 1 wt % hydrophobic modification. Associative polymers can comprise $C_{16}$ (palmityl) alkyl hydrophobic side chains with 0.7 wt % hydrophobic modification, but a percentage hydrophobic modification can be up to an aqueous solubility limit in surfactant compositions (e.g., up to 2 wt %, 5 wt %, or 10 wt %). Other associative polymers can include stearyl, octyl, decyl and lauryl side chains, alkyl acrylate polymers, polyacrylates, hydrophobically-modified polysaccharides, hydrophobically-modified urethanes, AQUPEC® SER-150 (acrylate/$C_{10}$-$C_{30}$ alkyl acrylate cross-polymer) comprising about Cis (stearyl) side chains and 0.4 wt % HM, and AQUPEC® HV-701EDR which comprises C8 (octyl) side chains and 3.5% HM, and mixtures thereof. Another exemplary associative polymer can be Stabylen 30 manufactured by 3V Sigma S.p.A., which has branched isodecanoate hydrophobic associative side chains.

As set forth above, the compositions herein can further include a non-associative polymer. Suitable non-associative polymers can include water-dispersible polymers with relatively uniform hydrophilic backbone lacking hydrophobic groups. Examples of non-associative polymers can include biopolymer polysaccharides (e.g., xanthan gum, gellan gum), cellulosic polysaccharides (e.g., carboxymethyl cellulose, carboxymethyl hydroxyethyl cellulose), other polysaccharides (e.g., guar gum, hydroxypropyl guar, and sodium alginate), and synthetic hydrocarbon polymers (e.g., polyacrylamide and copolymers, polyethylene oxide, polyacrylic acid copolymers).

Electrolyte

The compositions herein may comprise from 0.05% to 10%, by weight of composition, of an electrolyte. The electrolyte may comprise an anion selected from the group consisting of phosphate, chloride, sulfate, citrate, and mixtures thereof, and a cation selected from the group consisting of sodium, ammonium, potassium, magnesium, and mixtures thereof. The electrolyte may also be selected from the group consisting of sodium chloride, ammonium chloride, sodium sulfate, ammonium sulfate, and mixtures thereof. The composition may comprise a dermatologically acceptable moisturizer. Such dermatologically acceptable moisturizers an include lipids of natural and/or petroleum based sources. Lipids of natural sources can include various vegetable oils such as soybean oil, coconut oil, palm oil, palm stearine oil, canola oil, sunflower oil, and corn oil. Other such natural lipids contain various plant and extract butters such as shea butter, cocoa butter. Petroleum sources oils contain petrolatum and various mineral oils.

Carrier

The compositions herein may comprise a dermatologically acceptable carrier. Dermatologically acceptable carriers may be selected for various stability, aesthetics, and/or compatibility with other materials present in the composition. Suitable carriers include water and/or water soluble solvents. The composition may comprise from 1% to 95% by weight of water and/or water equivalent solvent. The composition may comprise from 1%, 3%, 5%, 10%, 15%, 20%, 25%, 30%, 35%, 40%, 45%, 50%, 55%, 60%, 65%, 70%, 75%, 80%, 85%, or 90% to 90%, 85%, 80%, 75%, 70%, 65%, 60%, 55%, 50%, 45%, 40%, 35%, 30%, 25%, 20%, 15%, 10%, or 5% water and/or a water-equivalent solvent, by weight of the composition. "Water-equivalent solvent" refers to a compound which has a similar ability as water to solubilize a material. Suitable water-equivalent solvents can include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, octanediol, ethylhexanediol, decanediol; glycerin; water, and mixtures thereof. A composition can comprise, for example, water, a diol, glycerin, or combinations thereof.

Suitable carriers also include oils. The composition may comprise from 1% to 95% by weight of one or more oils. Oils may be used to solubilize, disperse, or carry materials that are not suitable for water or water-equivalent solvents. Suitable oils can include silicones, hydrocarbons, esters, fatty amides, ethers, and mixtures thereof.

In one example, the composition further comprises water. Preferably the composition comprises at least 80 wt % water, more preferably 80-90 wt %, more preferably 83-90 wt % of the water.

Compositions

The compositions herein are liquid personal care cleaning compositions. Preferably the liquid personal care cleaning composition is selected from liquid hand washing composition, liquid body washing composition, liquid hair washing composition, and combinations thereof. Preferably the composition is a liquid hand washing composition. One example of a composition herein is a skin cleaning composition. The compositions herein can be single phase or multi-phase.

Another example of a liquid personal care cleaning composition is a hand sanitizer. A hand sanitizer is usually a leave on product. A hand sanitizer may comprise, for example, an alcohol, an antibacterial, a fragrance, surfactant, a colorant, beads, or any combination thereof. Alcohols for use herein can include, for example, ethanol, propanol, or a combination thereof. The alcohol may be present, for example, at a level of 30% to 80%, by weight of a hand sanitizing composition.

EXAMPLES

Inventive and comparative formulations examples are provided. Anti-microbial data demonstrating synergistic effect of linalool or linalool isomers in combination with hinokitiol is also provided.

TABLE 1

Hand washing compositions of the present inventions.

| Ingredients (100% active) | Preferred Ranges (Wt %) | Example 1 (Wt %) |
|---|---|---|
| Linalool | 0.8-1.2 | 0.9 |
| Hinokitiol | 0.08-0.25 | 0.1 |
| Linalool:Hinokitiol Ratio | 12:1 to 8:1 (wt:wt ratio) | 9:1 |
| Sodium Laureth 3 Sulfate | 4-9 | 6.5 |
| Sodium Lauryl Sulfate | 1-3 | 2.3 |
| Cocamidopropyl Betaine | 0.1-4 | 0.9 |
| Sodium benzoate | 0.4-0.6 | 0.5 |
| Benzyl alcohol | 0.4-1.0 | 0.9 |
| EDTA | 0.02-0.2 | 0.15 |
| Fragrance | 0.1-0.7 | 0.5 |
| Sodium chloride | 0-2.8 | 2.5 |
| Sodium salicylate | 0.2-0.6 | 0.5 |
| Citric acid | Adjust pH | Adjust pH |
| Purified water | Q.S. to 100 | Q.S. to 100 |
| pH | 4-5 | 4.0-5.0 |

Table 1 describes a non-limiting example of hand washing composition example 1. Preferred ranges of each of the ingredients is also provided.

TABLE 2A

Comparative Data containing Linalool and Hinokitiol (with only sodium lauryl sulfate as the surfactant, and at pH 4.5).

| Ingredients (100 wt % active) | Examples (Wt %) | | | |
|---|---|---|---|---|
| | A (Comparative) | B (Comparative) | C (Comparative) | 2 (Inventive) |
| Linalool | 0 | 0 | 0.90 | 0.90 |
| Hinokitiol | 0 | 0.10 | 0 | 0.10 |
| Sodium Laureth 3 Sulfate | 0 | 0 | 0 | 0 |
| Sodium Lauryl Sulfate | 9.0 | 9.0 | 9.0 | 9.0 |
| Cocamidopropyl Betaine | 0 | 0 | 0 | 0 |
| Sodium benzoate | 0.50 | 0.50 | 0.50 | 0.50 |
| Benzyl alcohol | 0.90 | 0.90 | 0.90 | 0.90 |
| EDTA | 0.15 | 0.15 | 0.15 | 0.15 |
| Fragrance | 0.50 | 0.50 | 0.50 | 0.50 |
| Sodium chloride | 2.50 | 2.50 | 2.50 | 2.50 |
| Sodium salicylate | 0.50 | 0.50 | 0.50 | 0.50 |
| Citric acid | Adjust pH | Adjust pH | Adjust pH | Adjust pH |
| Purified water | Q.S. to 100 | Q.S. to 100 | Q.S. to 100 | Q.S. to 100 |
| pH | 4.5 | 4.5 | 4.5 | 4.5 |
| Linalool:Hinokitiol Wt:Wt ratio | — | — | — | 9:1 |
| Total of Linalool and Hinokitiol | — | — | — | 1.00 |
| Total Surfactant | 9.00 | 9.00 | 9.00 | 9.00 |
| Bacteria Log Reduction[1] | 0.29 | 0.711 | 0.152 | 4.64 |

[1]Bacteria Log Reduction, the testing procedure thereof, is herein described. 8 mL of the subject composition is equilibrated to 20 degrees Celsius. 1 mL of 3 wt % Bovine Serum Albumin (BSA) is then added to the composition and mixed for 5 minutes. Bacteria inoculum (*E. coli*; ATCC 25922) is then prepared from a 24 hours culture plate at a concentration of $1 \times 10^{\wedge}8$ cfu/mL to $5 \times 10^{\wedge}8$ cfu/mL. 1 mL of the prepared inoculum is added to the product/BSA mixture and the fast kill time is started. The bacteria is mixed with the sample for a stipulated time of 2 minutes. After the stipulated time, 1 mL of the product/BSA/bacteria mixture is added into 9 mL of the neutralizer and mixed. The neutralizer is then incubated at room temperature (25 degrees Celsius) for 10 minutes, followed by serial dilution and plated out into Tryptic soy agar. The agar is then incubated at 37 degrees Celsius for 24-48 hours and then formed colonies are counted. Bacteria Log Reduction is calculated by measuring the *E. coli* inoculum concentration (CFU/ml) at the start of the experiment subtracting from *E. coli* concentration in the test reaction after the stipulated time. The same testing procedure for Bacteria Log Reduction was used for all of the data tables below.

Comparative examples A-C and inventive example 2 are described in Table 2A above. Only inventive example 2 contains both linalool and hinokitiol. Example A does not contain either of these ingredients while examples B and C contain only either hinokitiol or linalool, respectively. Synergy in inventive example 2 is demonstrated by much higher *E. coli* efficacy. The total surfactant level for all examples is at 9 wt %, containing only sodium lauryl sulfate surfactant.

TABLE 2B

Comparative Data containing Linalool and Hinokitiol (including SLS, SLES, and betaine surfactants, and at pH 4.5).

| Ingredients (100 wt % active) | Examples (Wt %) | | | |
|---|---|---|---|---|
| | D (Comparative) | E (Comparative) | F (Comparative) | 3 (Inventive) |
| Linalool | 0 | 0 | 0.90 | 0.90 |
| Hinokitiol | 0 | 0.10 | 0 | 0.10 |
| Sodium Laureth 3 Sulfate | 6.5 | 6.5 | 6.5 | 6.5 |
| Sodium Lauryl Sulfate | 9.0 | 2.3 | 2.3 | 2.3 |
| Cocamidopropyl Betaine | 0.9 | 0.9 | 0.9 | 0.9 |

TABLE 2B-continued

Comparative Data containing Linalool and Hinokitiol (including SLS, SLES, and betaine surfactants, and at pH 4.5).

| Ingredients (100 wt % active) | D (Comparative) | E (Comparative) | F (Comparative) | 3 (Inventive) |
|---|---|---|---|---|
| Sodium benzoate | 0.50 | 0.50 | 0.50 | 0.50 |
| Benzyl alcohol | 0.90 | 0.90 | 0.90 | 0.90 |
| EDTA | 0.15 | 0.15 | 0.15 | 0.15 |
| Fragrance | 0.50 | 0.50 | 0.50 | 0.50 |
| Sodium chloride | 2.50 | 2.50 | 2.50 | 2.50 |
| Sodium salicylate | 0.50 | 0.50 | 0.50 | 0.50 |
| Citric acid | Adjust pH | Adjust pH | Adjust pH | Adjust pH |
| Purified water | Q.S. to 100 | Q.S. to 100 | Q.S. to 100 | Q.S. to 100 |
| pH | 4.5 | 4.5 | 4.5 | 4.5 |
| Linalool:Hinokitiol Wt:Wt ratio | — | — | — | 9:1 |
| Total of Linalool and Hinokitiol | — | — | — | 1.00 |
| Total Surfactant | 9.70 | 9.70 | 9.70 | 9.70 |
| Bacteria Log Reduction | 0.29 | 0.711 | 0.152 | 4.64 |

Comparative examples D-F and inventive example 3 are described in Table 2B above. Only inventive example 3 contains both linalool and hinokitiol. Example D does not contain either of these ingredients, while examples E and F contain only either hinokitiol or linalool, respectively. Synergy in inventive example 3 is demonstrated by much higher *E. coli* efficacy. The total surfactant level for all examples is at 9.70 wt %, and all these examples contain betaine, sodium laureth 3 sulfate, and sodium lauryl sulfate surfactants. These samples are tested for visual stability, i.e., that over the course of one month there is visually no observed phase separation in these compositions.

TABLE 2C

Comparative Data containing Linalool and Hinokitiol (at pH 4.1).

| Ingredients (100 wt % active) | G (Comparative) | H (Comparative) | 4 (Inventive) |
|---|---|---|---|
| Linalool | 0 | 0.90 | 0.90 |
| Hinokitiol | 0.10 | 0 | 0.10 |
| Sodium Laureth 3 Sulfate | 6.5 | 6.5 | 6.5 |
| Sodium Lauryl Sulfate | 2.3 | 2.3 | 2.3 |
| Cocamidopropyl Betaine | 0.9 | 0.9 | 0.9 |
| Sodium benzoate | 0.50 | 0.50 | 0.50 |
| Benzyl alcohol | 0.90 | 0.90 | 0.90 |
| EDTA | 0.15 | 0.15 | 0.15 |
| Fragrance | 0.50 | 0.50 | 0.50 |
| Sodium chloride | 2.50 | 2.50 | 2.50 |
| Sodium salicylate | 0.50 | 0.50 | 0.50 |
| Citric acid | Adjust pH | Adjust pH | Adjust pH |
| Purified water | Q.S. to 100 | Q.S. to 100 | Q.S. to 100 |
| pH | 4.1 | 4.1 | 4.1 |
| Linalool:Hinokitiol Wt:Wt ratio | — | — | 9:1 |
| Total amount of Linalool and Hinokitiol | — | — | 1.00 |
| Total Surfactant | 9.70 | 9.70 | 9.70 |
| Bacteria Log Reduction | 0.25 | 2.26 | 5.16 |

Comparative examples G and H, and inventive example 4, are described in Table 2C above. Only inventive example 4 contains both linalool and hinokitiol. Examples G and H contain only either hinokitiol or linalool, respectively. Synergy in inventive example 4 is demonstrated by much higher *E. coli* efficacy. Much like the prior table, the total surfactant level for all examples are at 9.70 wt % and all examples contain betaine, sodium laureth 3 sulfate, and sodium lauryl sulfate surfactants. Notably, the examples in this Table 2C have a pH of 4.1 (which is lower than earlier examples).

TABLE 2D

Comparative Data containing Linalool and Hinokitiol (at pH 4.3).

| Ingredients (100 wt % active) | I (Comparative) | J (Comparative) | 5 (Inventive) |
|---|---|---|---|
| Linalool | 0 | 0.90 | 0.90 |
| Hinokitiol | 0.10 | 0 | 0.10 |
| Sodium Laureth 3 Sulfate | 6.5 | 6.5 | 6.5 |
| Sodium Lauryl Sulfate | 2.3 | 2.3 | 2.3 |
| Cocamidopropyl Betaine | 0.9 | 0.9 | 0.9 |
| Sodium benzoate | 0.50 | 0.50 | 0.50 |
| Benzyl alcohol | 0.90 | 0.90 | 0.90 |
| EDTA | 0.15 | 0.15 | 0.15 |
| Fragrance | 0.50 | 0.50 | 0.50 |
| Sodium chloride | 2.50 | 2.50 | 2.50 |
| Sodium salicylate | 0.50 | 0.50 | 0.50 |
| Citric acid | Adjust pH | Adjust pH | Adjust pH |
| Purified water | Q.S. to 100 | Q.S. to 100 | Q.S. to 100 |
| pH | 4.3 | 4.3 | 4.3 |
| Linalool:Hinokitiol Wt:Wt ratio | — | — | 9:1 |
| Total amount of Linalool and Hinokitiol | — | — | 1.00 |
| Total Surfactant | 9.70 | 9.70 | 9.70 |
| Bacteria Log Reduction | 0.14 | 1.05 | 3.83 |

Comparative examples I and J, and inventive example 5, are described in Table 2D above. Only inventive example 5 contains both linalool and hinokitiol. Examples I and J contain only either hinokitiol or linalool, respectively. Synergy in inventive example 5 is demonstrated by much higher *E. coli* efficacy. The total surfactant level for all examples is again at 9.70 wt % and all contain betaine, sodium laureth 3 sulfate, and sodium lauryl sulfate surfactants. Notably, the examples in this Table 2D have a pH of 4.3.

TABLE 2E

Comparative Data containing Linalool and Hinokitiol (at pH 4.7).

| Ingredients (100 wt % active) | K (Comparative) | L (Comparative) | 6 (Inventive) |
|---|---|---|---|
| Linalool | 0 | 0.90 | 0.90 |
| Hinokitiol | 0.10 | 0 | 0.10 |
| Sodium Laureth 3 Sulfate | 6.5 | 6.5 | 6.5 |
| Sodium Lauryl Sulfate | 2.3 | 2.3 | 2.3 |
| Cocamidopropyl Betaine | 0.9 | 0.9 | 0.9 |
| Sodium benzoate | 0.50 | 0.50 | 0.50 |
| Benzyl alcohol | 0.90 | 0.90 | 0.90 |
| EDTA | 0.15 | 0.15 | 0.15 |
| Fragrance | 0.50 | 0.50 | 0.50 |
| Sodium chloride | 2.50 | 2.50 | 2.50 |
| Sodium salicylate | 0.50 | 0.50 | 0.50 |

TABLE 2E-continued

Comparative Data containing Linalool and Hinokitiol (at pH 4.7).

| Ingredients (100 wt % active) | Examples (Wt %) | | |
|---|---|---|---|
| | K (Comparative) | L (Comparative) | 6 (Inventive) |
| Citric acid | Adjust pH | Adjust pH | Adjust pH |
| Purified water | Q.S. to 100 | Q.S. to 100 | Q.S. to 100 |
| pH | 4.7 | 4.7 | 4.7 |
| Linalool:Hinokitiol Wt:Wt ratio | — | — | 9:1 |
| Total amount of Linalool and Hinokitiol | — | — | 1.00 |
| Total Surfactant | 9.70 | 9.70 | 9.70 |
| Bacteria Log Reduction | 0.03 | 0.12 | 2.7 |

Comparative examples K and L, and inventive example 6, are described in Table 2E above. Only inventive example 6 contains both linalool and hinokitiol. Examples K and L contain only either hinokitiol or linalool, respectively. Synergy in inventive example 6 is demonstrated by much higher *E. coli* efficacy. Much like the prior table, the total surfactant level for all examples are at 9.70 wt % and all these examples contain betaine, sodium laureth 3 sulfate, and sodium lauryl sulfate surfactants. Notably, the examples in this Table 2E have a pH of 4.7 (which is the highest of the examples of Table 2A-2G).

TABLE 2F

Comparative Data containing Linalool and Hinokitiol (at varying ratios/concentration of Hinokitiol and Linalool, and at pH 4.5).

| Ingredients (100 wt % active) | Comparative | | | | | Inventive |
|---|---|---|---|---|---|---|
| | M | N | O | P | Q | 7 |
| Linalool | 0 | 0 | 0.90 | 0.10 | 0.50 | 0.90 |
| Hinokitiol | 0 | 0.10 | 0 | 0.10 | 0.10 | 0.10 |
| Sodium Laureth 3 Sulfate | 6.5 | 6.5 | 6.5 | 6.5 | 6.5 | 6.5 |
| Sodium Lauryl Sulfate | 2.3 | 2.3 | 2.3 | 2.3 | 2.3 | 2.3 |
| Cocamidopropyl Betaine | 0.9 | 0.9 | 0.9 | 0.9 | 0.9 | 0.9 |
| Sodium benzoate | 0.50 | 0.50 | 0.50 | 0.50 | 0.50 | 0.50 |
| Benzyl alcohol | 0.90 | 0.90 | 0.90 | 0.90 | 0.90 | 0.90 |
| EDTA | 0.15 | 0.15 | 0.15 | 0.15 | 0.15 | 0.15 |
| Fragrance | 0.50 | 0.50 | 0.50 | 0.50 | 0.50 | 0.50 |
| Sodium chloride | 2.50 | 2.50 | 2.50 | 2.50 | 2.50 | 2.50 |
| Sodium salicylate | 0.50 | 0.50 | 0.50 | 0.50 | 0.50 | 0.50 |
| Citric acid | Adjust pH | | | | | |
| Purified water | Q.S. to 100 | | | | | |
| pH | 4.5 | 4.5 | 4.5 | 4.5 | 4.5 | 4.5 |
| Linalool:Hinokitiol Wt:Wt ratio | — | — | — | 1:1 | 5:1 | 9:1 |
| Total of Linalool and Hinokitiol | 0 | 0.10 | 0.90 | 0.20 | 0.50 | 1.00 |
| Total Surfactant | 9.70 | 9.70 | 9.70 | 9.70 | 9.70 | 9.70 |
| Bacteria Log Reduction | 0.04 | 0.08 | 0.49 | 0.17 | 0.12 | 4.64 |

Comparative examples M-Q, and inventive example 7, are described in Table 2F above. Comparative example M does not contain either linalool or hinokitiol (control), and comparative examples N and O contain only either hinokitiol or linalool, respectively. Comparative examples P and Q as well as inventive example 7 each contain both linalool and hinokitiol. However, comparative examples P and Q contain less than 0.8 wt % of the combination of both hinokitiol and linalool to report unacceptable *E. coli* efficacy. On the other hand, inventive example 7 has greater than 0.8 wt % (at 1 wt %) of both linalool and hinokitiol and a wt:wt ratio therein between of 9:1. Synergy in inventive example 7 is demonstrated by much higher *E. coli* efficacy. Again, the total surfactant level for all examples are at 9.70 wt % and these examples contain betaine, sodium laureth 3 sulfate, and sodium lauryl sulfate as surfactants. Notably, the examples in this Table 2F have a pH of about 4.5.

TABLE 2G

Comparative Data containing Linalool and Hinokitiol (at varying ratios/concentration of Hinokitiol and Linalool at pH 4.5).

| Ingredients (100 wt % active) | Examples (Wt %) | | |
|---|---|---|---|
| | R (Comparative) | S (Comparative) | 8 (Inventive) |
| Linalool | 0.72 | 0.90 | 0.81 |
| Hinokitiol | 0.08 | 0.05 | 0.09 |
| Sodium Laureth 3 Sulfate | 6.5 | 6.5 | 6.5 |
| Sodium Lauryl Sulfate | 2.3 | 2.3 | 2.3 |
| Cocamidopropyl Betaine | 0.9 | 0.9 | 0.9 |
| Sodium benzoate | 0.50 | 0.50 | 0.50 |
| Benzyl alcohol | 0.90 | 0.90 | 0.90 |
| EDTA | 0.15 | 0.15 | 0.15 |
| Fragrance | 0.50 | 0.50 | 0.50 |
| Sodium chloride | 2.50 | 2.50 | 2.50 |
| Sodium salicylate | 0.50 | 0.50 | 0.50 |
| Citric acid | Adjust pH | Adjust pH | Adjust pH |
| Purified water | Q.S. to 100 | Q.S. to 100 | Q.S. to 100 |
| pH | 4.5 | 4.5 | 4.5 |
| Linalool:Hinokitiol Wt:Wt ratio | 9:1 | 18:1 | 9:1 |
| Total amount of Linalool and Hinokitiol | 0.80 | 0.90 | 0.90 |
| Total Surfactant | 9.70 | 9.70 | 9.70 |
| Bacteria Log Reduction | 0.48 | 0.30 | 1.40 |

Referring to Table 2G, comparative examples R and S, and inventive example 8 each contain both linalool and hinokitiol. Comparative example R has a desirable linalool:hinokitiol weight ratio; however, there is only 0.80 wt % of a total amount of linalool and hinokitiol. Consequently, the *E. coli* efficacy of example R is not acceptable. Comparative example S has a desirable total amount of linalool and hinokitiol at 0.90 wt %; however, the linalool: hinokitiol weight ratio is at 18:1. Consequently, the *E. coli* efficacy of example S is not acceptable. Only inventive example 8 has the desirable combination of linalool: hinokitiol weight ratio and total amount of linalool and hinokitiol at 9:1 and 0.90 wt %, respectively. Again, the total surfactant level for all examples is 9.70 wt % and contain betaine, sodium laureth 3 sulfate, and sodium lauryl sulfate surfactants. Notably, the examples in this Table 2G have a pH of 4.5.

TABLE 3

Comparative Data containing Geraniol and Hinokitiol.

| Ingredients (100 wt % active) | Examples (Wt %) | | | |
|---|---|---|---|---|
| | T (Comparative) | U (Comparative) | V (Comparative) | 9 (Inventive) |
| Geraniol | 0 | 0 | 0.90 | 0.90 |
| Hinokitiol | 0 | 0.10 | 0 | 0.10 |
| Sodium Laureth 3 Sulfate | 6.5 | 6.5 | 6.5 | 6.5 |

TABLE 3-continued

Comparative Data containing Geraniol and Hinokitiol.

| Ingredients (100 wt % active) | T (Comparative) | U (Comparative) | V (Comparative) | 9 (Inventive) |
|---|---|---|---|---|
| Sodium Lauryl Sulfate | 2.3 | 2.3 | 2.3 | 2.3 |
| Cocamidopropyl Betaine | 0.9 | 0.9 | 0.9 | 0.9 |
| Sodium benzoate | 0.50 | 0.50 | 0.50 | 0.50 |
| Benzyl alcohol | 0.90 | 0.90 | 0.90 | 0.90 |
| EDTA | 0.15 | 0.15 | 0.15 | 0.15 |
| Fragrance | 0.50 | 0.50 | 0.50 | 0.50 |
| Sodium chloride | 2.50 | 2.50 | 2.50 | 2.50 |
| Sodium salicylate | 0.50 | 0.50 | 0.50 | 0.50 |
| Citric acid | Adjust pH | Adjust pH | Adjust pH | Adjust pH |
| Purified water | Q.S. to 100 | Q.S. to 100 | Q.S. to 100 | Q.S. to 100 |
| pH | 4.5 | 4.5 | 4.5 | 4.5 |
| Geraniol:Hinokitiol Wt:Wt ratio | — | — | — | 9:1 |
| Total of Geraniol and Hinokitiol | | | | 1.00 |
| Total Surfactant | 9.70 | 9.70 | 9.70 | 9.70 |
| Bacteria Log Reduction | 0.04 | 0.08 | 0.70 | 3.99 |

Comparative examples T, U, and V, and inventive example 9, are described in Table 3 above. Example T does not contain either geraniol and hinokitiol, while examples U and V contain only either hinokitiol or geraniol, respectively. Only inventive example 9 contains both geraniol and hinokitiol. Synergy in inventive example 9 is demonstrated by much higher *E. coli* efficacy. Again, the total surfactant level for all examples are at 9.70 wt % and these examples contain betaine, sodium laureth 3 sulfate, and sodium lauryl sulfate surfactants. The examples all have a pH of 4.5.

TABLE 4

Comparative Data containing Nerol and Hinokitiol.

| Ingredients (100 wt % active) | W (Comparative) | X (Comparative) | Y (Comparative) | 10 (Inventive) |
|---|---|---|---|---|
| Nerol | 0 | 0 | 0.90 | 0.90 |
| Hinokitiol | 0 | 0.10 | 0 | 0.10 |
| Sodium Laureth 3 Sulfate | 6.5 | 6.5 | 6.5 | 6.5 |
| Sodium Lauryl Sulfate | 2.3 | 2.3 | 2.3 | 2.3 |
| Cocamidopropyl Betaine | 0.9 | 0.9 | 0.9 | 0.9 |
| Sodium benzoate | 0.50 | 0.50 | 0.50 | 0.50 |
| Benzyl alcohol | 0.90 | 0.90 | 0.90 | 0.90 |
| EDTA | 0.15 | 0.15 | 0.15 | 0.15 |
| Fragrance | 0.50 | 0.50 | 0.50 | 0.50 |
| Sodium chloride | 2.50 | 2.50 | 2.50 | 2.50 |
| Sodium salicylate | 0.50 | 0.50 | 0.50 | 0.50 |
| Citric acid | Adjust pH | Adjust pH | Adjust pH | Adjust pH |
| Purified water | Q.S. to 100 | Q.S. to 100 | Q.S. to 100 | Q.S. to 100 |
| pH | 4.5 | 4.5 | 4.5 | 4.5 |
| Nerol:Hinokitiol Wt:Wt ratio | — | — | — | 9:1 |
| Total of Nerol and Hinokitiol | | | | 1.00 |
| Total Surfactant | 9.70 | 9.70 | 9.70 | 9.70 |
| Bacteria Log Reduction | 0.04 | 0.08 | 0.82 | 6.20 |

Comparative examples W, X, and Y, and inventive example 10, are described in Table 4 above. Example W does not contain either nerol and hinokitiol, while examples U and V contain only hinokitiol and nerol, respectively. With respect to Table 3, only inventive example 10 contains both nerol and hinokitiol. Synergy in inventive example 10 is demonstrated by much higher *E. coli* efficacy. Again, the total surfactant level for all examples are at 9.70 wt % and examples contain betaine, sodium laureth 3 sulfate, and sodium lauryl sulfate surfactants. The examples all have a pH of 4.5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antibacterial liquid personal care cleaning composition comprising:
   (a) greater than 4 wt % of at least one anionic surfactant;
   (b) greater than 0.8 wt % to 2.0 wt % of a combination of:
      (i) linalool, a linalool isomer, or combinations thereof; and (ii) hinokitiol;
   (c) wherein the weight: weight ratio said linalool, linalool isomer(s), or combinations thereof to said hinokitiol is less than 18:1; and (d) pH is less than 7;
wherein the composition exhibits effective antibacterial properties.

2. The composition of claim 1, wherein the weight:weight ratio said linalool, linalool isomer(s), or combinations thereof to said hinokitiol is less than 15:1.

3. The composition of claim 2, wherein the weight:weight ratio said linalool, linalool isomer(s), or combinations thereof to said hinokitiol is from 13:1 to 1:1.

4. The composition of claim 1, wherein the composition comprises greater than 0.05 wt % but less than 1 wt % of hinokitiol.

5. The composition of claim 4, wherein the composition comprises at least 0.1 wt % to 0.5 wt % of hinokitiol.

6. The composition of claim 1, wherein the composition comprises at least 0.1 wt % of said linalool, a linalool isomer, or combinations thereof.

7. The composition of claim 6, wherein the composition comprises from at least 0.5 wt % of said linalool, a linalool isomer, or combinations thereof.

8. The composition of claim 1 comprising less than 1 wt % hinokitiol.

9. The composition of claim 8 comprising less than 0.5 wt % hinokitiol.

10. The composition of claim 1, wherein the composition comprises greater than 7 wt % of the at least one anionic surfactant.

11. The composition of claim 1, wherein the at least one anionic surfactant comprises at least a first alkyl sulfate surfactant and a second alkyl sulfate surfactant.

12. The composition of claim 1, wherein the at least one anionic surfactant comprises at least an alkyl sulfate surfactant.

13. The composition of claim 1, wherein the pH is from 4 to 5.2.

14. The composition of claim 1, wherein the linalool isomer is selected from geraniol, nerol, and combination thereof.

15. The composition of claim 1, wherein the composition further comprises a betaine.

16. The composition of claim 1, wherein the composition further comprises at least 80 wt % water.

17. The composition of claim 1, wherein the liquid personal care cleaning composition is selected from liquid hand washing composition, liquid body washing composition, liquid hair washing composition, and combinations thereof.

18. The composition of claim 17, wherein the liquid personal care cleaning composition is a liquid hand washing composition.

19. The composition of claim 1, wherein the composition comprises:
(a) from at least 0.1 wt % to less than 0.3 wt % of hinokitiol;
(b) from at least 0.8 wt % to less than 1.2 wt % of said linalool, a linalool isomer, or combinations thereof;
(c) greater than 7 wt % of the at least one anionic surfactant;
(d) from pH 4 to 5; and
(e) wherein the weight:weight ratio said linalool, linalool isomer(s), or combinations thereof to said hinokitiol is from 12:1 to 5:1, respectively.

20. The composition of claim 19, wherein the composition comprises:
(a) about 0.1 wt % hinokitiol; and
(b) about 0.9 wt % linalool of said linalool, a linalool isomer, or combinations thereof.

* * * * *